United States Patent [19]

Kirby et al.

[11] Patent Number: 4,927,833

[45] Date of Patent: May 22, 1990

[54] SUBSTITUTED AZOLES AND THEIR USE AS FUNGICIDES

[75] Inventors: Neil V. Kirby, Wantage; Peter F. S. Street, Burbage, both of Great Britain; Lowell D. Markley, Midland, Mich.

[73] Assignee: The Dow Chemical Company, Midland, Mich.

[21] Appl. No.: 299,911

[22] Filed: Jan. 23, 1989

[51] Int. Cl.[5] .................... C07D 233/60; A01N 43/50

[52] U.S. Cl. .................................... 514/399; 514/184; 548/101; 548/341; 548/267.8; 548/268.6

[58] Field of Search ................ 548/101, 341, 184, 399

[56] References Cited

U.S. PATENT DOCUMENTS

| | | | |
|---|---|---|---|
| 4,507,140 | 3/1985 | Sugavanam | 514/399 |
| 4,634,466 | 1/1987 | Noon et al. | 71/92 |

*Primary Examiner*—Glennon H. Hollrah
*Assistant Examiner*—Patricia L. Morris
*Attorney, Agent, or Firm*—S. Preston Jones; Ronald G. Brookens

[57] ABSTRACT

Substituted azole compounds especially substituted imidazole and triazole compounds, their preparation, compositions containing said compounds and the use of said compositions to control fungal infections in plants are disclosed.

21 Claims, No Drawings

SUBSTITUTED AZOLES AND THEIR USE AS FUNGICIDES

FIELD OF THE INVENTION

The present invention is directed to substituted azole compounds especially substituted imidazole and triazole compounds, compositions containing said compounds and the use of said compositions to control fungal infections in plants.

SUMMARY OF THE INVENTION

The present invention is directed to substituted imidazole and triazole compounds corresponding to the formulae

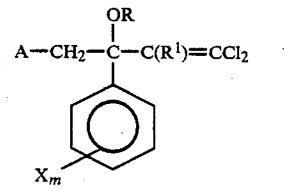
(I)

wherein

A represents

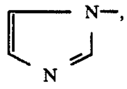 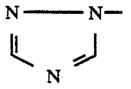 or 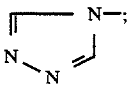

R represents —H, $C_1$–$C_4$ alkyl, $C_1$–$C_4$ alkenyl, $C_1$–$C_4$ haloalkyl or —C(O)$R^2$;

$R^1$ represents —H, halo or $C_1$–$C_4$ straight chain alkyl;

$R^2$ represents $C_1$–$C_4$ alkyl, $C_1$–$C_2$ haloalkyl, phenyl, or substituted phenyl;

each X independently represents —H, halo, —CN, $C_1$–$C_4$ alkyl, $C_1$–$C_4$ haloalkyl, $C_1$–$C_4$ alkoxy, $C_1$–$C_4$ alkylsulfonyloxy, nitro or phenyl;

m represents 1 to 5; and the acid addition salts and metal complexes thereof.

In addition, the present invention is directed to compositions containing compounds of Formula I as an active ingredient therein, and to methods of using said compositions in the kill and control of plant fungi.

In the present specification and claims, the term "alkyl" designates straight or branched chain alkyl groups such as methyl, ethyl, propyl (n- or -iso) and butyl (n-, secondary, iso or tertiary).

In the present specification and claims, the term "halo" designates bromo, chloro or fluoro atoms.

In the present specification and claims, the term "haloalkyl" designates an alkyl group as defined above which is substituted with from at least one (1) bromo, chloro or fluoro atom up to perbromo-, perchloro or perfluoro substituents including mixtures thereof, such as for example, chloromethyl, dichloromethyl, trichloromethyl, 1-chloroethyl, 1-chloro-n-propyl, perfluoro-n-butyl and the like.

The term "substituted phenyl" includes, but is not limited to, lower alkylphenyl such as methylphenyl, dimethylphenyl, trimethylphenyl, ethylphenyl, diethylphenyl, triethylphenyl, methylethylphenyl, dimethylethylphenyl, propylphenyl, butylphenyl, pentylphenyl, hexylphenyl; and halophenyl, such as mono, di, tri, tetra or pentahalophenyl.

The active ingredients of Formula I wherein R represents —H or —C(O)$R^2$, $R^1$ is —H, $R^2$ is alkyl or haloalkyl, and X is —H or halo constitutes a preferred embodiment. The active ingredients of Formula I wherein m is 0, 1 or 2 constitutes a more preferred embodiment. The active ingredients of Formula I wherein R represents —H, $R^1$ is —H, and X is —H or halo constitutes a most preferred embodiment.

In the present invention, it is to be noted that all substituent groups are sterically compatible with each other. The term "sterically compatible" is employed to designate substituent groups which are not affected by steric hindrance as this term is defined in *The Condensed Chemical Dictionary*, 7th edition, Reinhold Publishing Co., N.Y. page 893 (1966) which definition is as follows:

> "steric hindrance. A characteristic of molecular structure in which the molecules have a spatial arrangement of their atoms such that a given reaction with another molecule is prevented or retarded in rate."

Sterically compatible may be further defined as reacting compounds having substituents whose physical bulk does not require confinement within volumes insufficient for the exercise of their normal behavior as discussed in *Organic Chemistry* of D. J. Cram and G. Hammond, 2nd edition, McGraw-Hill Book Company, N.Y., page 215 (1964).

The compounds of the present invention contain the asymmetrical active center designated by "*"

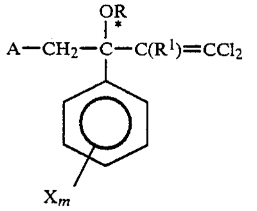
(I)

and can exist in optically active stereoisomeric forms such as the R and S enantiomeric forms. The use of the various mixtures and racemates of the above isomers are within the scope of the present invention. Additionally, one of the enantiomers of such compounds may be found to be more active biologically than the other enantiomer and the more active enantiomer, isolated by conventional procedures, may be used whenever the greater activity justifies any extra expenses which may occur from the use of said isomer.

In addition, the compounds of the present invention can contain isomers of the geometric isomer class which result from a carbon-carbon double bond. The resulting isomers are called cis (Z) and trans (E) isomers.

A general discussion of the isomer activity difference phenomenon can be found in A. Albert, *Selective Toxicity*, 4th edition, Met Luen & Co., Ltd., London, 1968, pp. 387–390 and more particular discussions in A. Fredga and B. Åberg, "Stereoisomerism in plant growth regulators of the auxin type", Ann. Rev. Plant Physiology 16:53–72, 1965, and in E. J. Lien, J. F. R. DeMiranda and E. J. Airens, "Quantitative structure-activity correlation of optical isomers", Molecular Pharmacology 12:598–604, 1976.

The compounds of the present invention are generally crystalline solids at ambient temperatures which are soluble in many organic solvents.

The acid addition salts can be salts of an inorganic or organic acid, such as, for example, hydrochloric, nitric, sulfuric, acetic, 4-toluene sulfonic or oxalic acid.

The metal complexes have the formula $$[M[X]_n]A_p \cdot zH_2O \quad (II)$$

wherein

- M represents copper, zinc, manganese or iron;
- X represents compound of Formula I;
- A represents an anion (e.g. chloride, bromide, iodide, nitrate, sulfate or phosphate anion);
- n represents the integer 2 or 4;
- p is an integer which corresponds to the valence of M; and
- z represents an integer of from 0 to 12.

Representative compounds which correspond to Formula I include the compounds set forth below in Table I.

TABLE 1

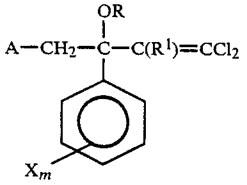

(I)

| A | R | $R^1$ | $X_m$ |
|---|---|---|---|
| 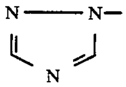 | H | H | H |
| " | H | H | 3,5-dichloro |
| " | $CH_3$ | H | 3,5-dibromo |
| " | H | Br | H |
| " | H | Cl | 3,5-$CF_3$ |
| " | H | H | 4-$C_3H_6CF_3$ |
| " | $C_2H_4$ | H | 4-$CF_2Cl$ |
| " | H | H | 4-Cl |
| " | H | $CH_3$ | 4-Cl |
| " | H | $C_4H_9$ | 4-Cl |
| " | H | H | 2,4-difluoro |
| " | H | H | 4-Cl |
| 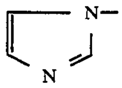 | H | H | 3,5-dichloro |
| | H | H | 4-fluoro |
| | $CH_3$ | H | pentachloro |
| 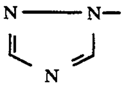 | $C(O)CF_3$ | H | 4-Cl |
| | H | H | 4-$NO_2$ |
| | H | H | 3-$NO_2$ |
| " | H | H | 4-Cl |
| " | H | H | 4-F |
| " | H | H | 4-Br |
| 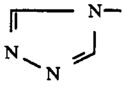 | H | H | 3,5-dichloro |
| | $CF_3$ | Cl | 4-$CH_3SO_2$—O— |
| 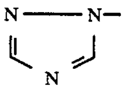 | H | H | 2,4-dichloro |
| " | H | H | 4-tertbutyl |
| " | H | H | H |
| " | H | H | 4-phenyl |
| " | H | H | 4-methyl |
| " | $C(O)CH_3$ | H | 4-Cl |

TABLE 1-continued

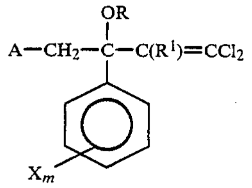

(I)

| A | R | $R^1$ | $X_m$ |
|---|---|---|---|
| " | $C(O)C_4H_9$ | $C_2H_5$ | 3,5-dimethyl |

The compounds of the present invention can be prepared by a variety of methods. The compounds wherein R is hydrogen and A is triazole can be prepared by the reaction of an appropriate oxirane reactant, corresponding to Formula III:

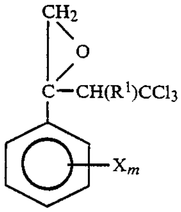

(III)

where X and m are as defined hereinabove, with sodium 1,2,4-triazole in the presence of acetic acid at a temperature of from about 75° about 110° C. When this preparative procedure is employed, both the asymmetrical and symmetrical triazole isomer products are obtained. If desired, these two products can be separated from each other employing conventional separation techniques, such as, for example, high pressure liquid chromatography.

In another procedure for preparing compounds wherein R is hydrogen; A is triazole and there is no X substitution in the number 2 ring position, the appropriate oxirane reactant of Formula III is reacted at ambient temperatures with an alkali metal salt of 1,2,4-triazole in the presence of a $C_1$–$C_4$ lower alkanol. The desired solid product can then be recovered employing conventional separatory techniques such as, filtration, decantation and the like. The product, if desired, can be further purified employing conventional techniques such as, solvent recrystallization. When this procedure is employed, only the asymmetrical triazole product is obtained.

The compounds wherein R is —$C(O)R^2$ and A is triazole can be prepared by reacting, at room temperature, an appropriate compound of Formula I wherein R is hydrogen with an appropriate acid anhydride of the formula $O(C(O)R^2)_2$ wherein $R^2$ is as defined hereinabove in a solvent, such as, for example, benzene, chloroform, methylene chloride, ethyl acetate or the like, and in the presence of a catalyst, such as, for example, 4-dimethylaminopyridine. The product can be recovered employing conventional separatory procedures.

The salts and metal complexes of the compounds of Formula I can be prepared from the latter employing conventional procedures. The salts are obtained by mixing an appropriate organic or inorganic acid with the compound of Formula I, if necessary in an inert solvent, distilling off the solvent and recrystallizing the residue as necessary. Alternately, water soluble salts such as phosphates and acetates may be prepared as aqueous solutions, for ease of formulation, by neutralization of the compound in an equimolar amount of the acid. Oil soluble acid derivatives such as the oleate may also be prepared by a similar means in an organic solvent such as xylene. The complexes, for example, can be prepared by reacting the uncomplexed compound with an appropriate metal salt in the presence of a suitable solvent.

The following Examples illustrate the present invention and the manner by which it can be practiced, but as such, should not be construed as limitations upon the overall scope of the same.

EXAMPLE I 1,1-Dichloro-3-(3,5-dichlorophenyl)-3-hydroxy-4-(1,2,4-(1H)triazolyl)but-1-ene

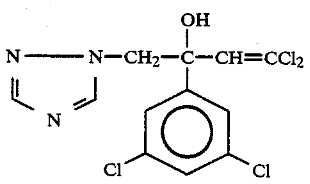

A solution was prepared by adding 3.46 g (0.053 mol) of 1,2,4-triazole to a mixture of 1.21 g of sodium metal dissolved in 75 mL of methanol. To this solution was added 5.61 g (0.018 mol) of 1-(3,5-dichlorophenyl)-1-(2,2,2-trichloroethyl)oxirane.

The mixture was stirred at room temperature for 5 days. Seventy five (75) mL of water was added to the reaction mixture and the crude product was recovered by filtration. The crude product was dried in vacuo and recrystallized from a substantially 1:1 benzene-hexane mixture to give the above named compound, as white crystals, in a yield of 4.3 g (63 percent of theoretical), melting at 157° C.

| Elemental Analysis | % C | % H | % N |
|---|---|---|---|
| Calculated for $C_{12}H_9Cl_4N_3O$: | 40.46 | 2.47 | 11.86 |
| Found: | 40.83 | 2.57 | 11.90 |

By following the preparative procedures of Example I, the following compound was prepared:

1,1-Dichloro-3-(2,4-dichlorophenyl)-3-hydroxy-4-(1,2,4-(1H)-triazolyl)but-1-ene; yield 30%, melting point 137° C.

EXAMPLE II 1,1-Dichloro-3-(4-chlorophenyl)-3-hydroxy-4-(1,2,4-(1H)-triazolyl)but-1-ene

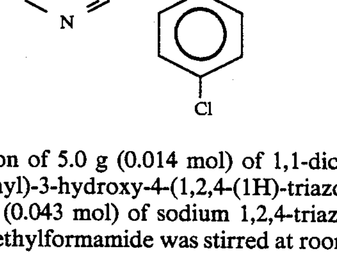

A solution of 5.0 g (0.014 mol) of 1,1-dichloro-3-(4-chlorophenyl)-3-hydroxy-4-(1,2,4-(1H)-triazolyl)butane and 3.85 g (0.043 mol) of sodium 1,2,4-triazolide in 75 mL of dimethylformamide was stirred at room temperature for 28 hours. To this solution was added 200 mL of water and 200 mL of diethyl ether. The organic phase was separated from the aqueous phase and then washed thrice with 100 mL portions of water and then dried over anhydrous sodium sulfate. The solvent was removed by evaporation under reduced pressure to give a yellow oil which solidified on standing overnight. This material was recrystallized from benzene to give the above named product in a yield of 2.6 g (58 percent of theoretical), melting at 95°-99° C.

| Elemental Analysis | % C | % H | % N |
|---|---|---|---|
| Calculated for $C_{12}H_{10}Cl_3N_3O$: | 45.24 | 3.16 | 13.19 |
| Found: | 45.18 | 3.10 | 13.06. |

EXAMPLE III 1,1-Dichloro-3-(3,5-dichlorophenyl)-3-hydroxy-4-(1H)imidazolyl)but-1-ene

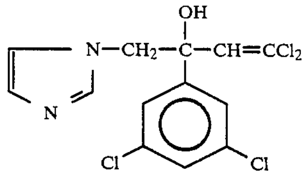

A mixture of 10.0 g (0.031 mol) of 1-(3,5-dichlorophenyl)-1-(2,2,2-trichloroethyl) oxirane, 5.0 g (0.036 mol) of 1-trimethylsilylimidazole and 10 mL of dimethylsulfoxide was stirred and heated under nitrogen at 80° C. for six hours.

The reaction mixture was poured into 100 mL of 10% hydrochloric acid and allowed to stand at room temperature for one hour.

This mixture was washed thrice with 50 mL portions of dichloromethane and the solution neutralized with aqueous sodium carbonate. The precipitate which formed was collected by filtration, washed with water, dried and recrystallized from benzene to give the desired product in a yield of 2.4 g (20 percent of theoretical), melting at 165° C.

By following the preparative procedures of Example II, the following compounds are prepared:

1,1-Dichloro-3-(3,5-dichlorophenyl)-3-hydroxy-4-((1H)-imidazolyl)but-1-ene; yield 65%, melting point 165° C.

1,1-Dichloro-3-(4-fluorophenyl)-3-hydroxy-4-((1H)-imidazolyl)but-1-ene; yield 50%, melting point 177° C.

It has been found that the compounds of Formula I have a high degree of fungicidal activity. The compounds are especially effective in the kill and control of fungal organisms which attack plants. Representative fungal disease organisms controlled include:

*Alternaria brassicicola* (leaf spot of brassicas),
*Alternaria tenuis* (leaf spot),
*Botrytis cinerea* (grey mold),
*Cochliobolus sativus* (spot blotch),
*Colletotrichum coffeanum* (coffee berry disease),
*Colletotrichum lindemuthianum* (anthracnose of bean),
*Erysiphe graminis hordeii* (wheat powdery mildew),
*Erysiphe graminis tritici* (barley powdery mildew),
*Fusarium culmorum* (head blight),
*Fusarium oxysporum fsp phaseolicola,*

*Gerlachia nivalis* (snow mold),
*Phytophthora citricola,*
*Phytophthora parasitica* (black shank),
*Plasmopara viticola* (grape downy mildew),
*Podosphaera leucotricha* (apple powdery mildew),
*Pseudocercosporella herpotrichoides* (cereal eye spot),
*Puccinia recondita* (brown rust),
*Pyrenophpora teres* (net blotch of barley),
*Pyricularia oryzae* (rice blast),
*Pythium ultimum* (damping off),
*Rhizoctonia cerealis* (sharp eye spot of wheat),
*Rhizoctonia solani* (root rot),
*Rhychosporium secalis* (leaf scald),
*Septoria ssp* (cereal leaf spot),
*Sclerotium rolfsii* (white rot),
*Sclerotinia sclerotiorum,*
*Verticillium albo-atrum* (wilt of tomatoes) and
*Venturia inaequalis* (apple scab).

Compositions containing the present compounds can be applied to the roots, seeds or foliage of the plants and will kill or control the growth of various fungi without damaging the commercial value of said plants. Many of these compositions are unique because of their systemic action and because of the very low levels of chemical required to control the fungal organism.

These chemicals may be prepared as dusts, wettable powders, flowable concentrates, suspension concentrates or emulsifiable concentrates.

The present invention includes within its scope a method for the control of fungus diseases attacking plants or plant parts which method comprises applying to the plants, the plant parts or to the organisms or to their habitats compositions containing one or more of the active compounds.

Another advantage of the present invention is that a single application of the compositions can provide a residual control of the fungal diseases over an extended period. Also, the compounds can be effective in eliminating established fungal infestations. Furthermore, many compounds have been found to be translocated in plants and, thus, can provide a systemic protection.

The method of the present invention comprises contacting plants, especially cereal grain plants, with a fungicidal amount of a composition containing one or more of the active compounds. The present invention also embraces the employment of a liquid, powder, dust or granular composition containing one or more of the active compounds in intimate admixture with inert, nonphytotoxic materials, known in the art as agricultural adjuvants and/or carriers, in solid or liquid form.

Thus, for example, the active compound(s) can be admixed with one or more additives including organic solvents, petroleum distillates, water or other liquid carriers, surface active dispersing agents, and finely divided inert solids. In such compositions, the active ingredients are present in a concentration from about 2.0 percent to about 95.0 percent by weight preferably 5.0 percent to about 95.0 percent by weight and most advantageously 5.0 percent to about 75.0 percent by weight.

The compound can be employed in the form of diluted flowable/suspension concentrates or a wettable powder composition containing 2 to 10,000 ppm of one or more of the compounds, preferably 10 to 600 ppm are employed. When the carrier contains a surface active agent, from about 0.1 to about 20.0 percent by weight of the active ingredient is advantageously employed. Depending upon the concentration in the composition, such augmented compositions are adapted to be employed for the control of the undesirable fungi or employed as concentrates and subsequently diluted with additional inert carrier, e.g. water, to produce the ultimate treating compositions.

In general, good results can be obtained with liquid compositions containing from about 0.0001 to about 2.0 percent by weight of the toxicant in the final diluted form. With dusts, good results can usually be obtained with compositions containing from about 0.1 to about 2.0 percent or more by weight of toxicant. Where the compositions are to be applied to foliage of plants to control the fungal organism, it is preferred that the toxicant be present in an amount not to exceed about 0.8 percent in liquid compositions and about 1.0 percent in dusts.

In terms of hectare application, good controls can be obtained when the active ingredients are applied to growing plants at a dosage of from about 0.004 to about 4.0 kg/hectare.

When employed as fungicides for the treatment of seeds or non-living substrates, from about 0.05 to about 1.0 gram of the active compound per kilogram of substrate is an effective dose.

In the preparation of dust, or wettable powder compositions, the toxicant products can be compounded with any of the finely divided solids, such as prophyllite, talc, chalk, gypsum, fuller's earth, bentonite, attapulgite, starch, casein, gluten, or the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures. Dust compositions are advantageously employed when treating seeds.

Granular formulations are usually prepared by impregnating a solution of the toxicant in a volatile organic solvent onto a bed of coarsely divided attapulgite, bentonite, diatomite, or the like.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions which may optionally contain water miscible organic co-solvents to improve the physical properties of the formulation. In such compositions, the carrier comprises an aqueous emulsion, i.e., a mixture of inert water-immiscible solvent and optional water miscible organic co-solvent, emulsifying agent, and water.

Emulsifiers which can be advantageously employed herein can be readily determined by those skilled in the art and include various nonionic and anionic emulsifiers, or a blend of two or more of said emulsifiers.

Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxide or mixtures of ethylene and propylene oxides such as the ethoxylated alkyl phenols and carboxylic esters solubilized with a polyol or polyoxyalkylene.

Anionic emulsifiers include the oil-soluble salts (e.g., calcium) of alkylaryl sulfonic acids, oil soluble salts of sulfated polyglycol ethers and appropriate salts of phosphated polyglycol ether.

The preferred emulsifiers will depend upon the nature of the emulsifiable concentrate and the desired use of said concentrate; the selection of the specific emulsifier follows conventional formulation practices and is well known to those skilled in the art. For example, an emulsifiable concentrate of a compound of Formula I containing 200 g/L of the compound in xylene may require a blend of an ethoxylated nonyl phenol and calcium dodecyl benzene sulphonate to function effectively whereas a similar emulsifiable concentrate of the oleate salt of a compound of Formula I soluble in an aliphatic organic solvent will require a considerably different emulsification system.

Representative organic liquids which can be employed in preparing the emulsifiable concentrates of the present invention are the aromatic liquids such as xylene; propyl benzene fractions; or mixed naphthalene fractions; mineral oils; substituted aromatic organic liquids such as dioctyl phthalate; kerosene; butene; dialkyl amides of various fatty acids, particularly the dimethyl amides of fatty glycols and glycol derivatives such as the n-butyl ether, ethyl ether or methyl ether of diethylene glycol, the methyl ether of triethylene glycol and ketones such as cyclohexanone, isophorone and dihydroisophorone. Mixtures of two or more organic liquids are also often suitably employed in the preparation of the emulsifiable concentrate. The preferred organic liquids are ketones, especially isophorone-xylene mixtures, xylene, and propyl benzene fractions, with xylene being most preferred.

The surface active dispersing agents are usually employed in liquid compositions and in the amount of from 0.1 to 20.0 percent by weight of the combined weight of the dispersing agent and active compound.

The active compositions can also contain other compatible additaments, for example, plant growth regulators and other biologically active compounds used in agriculture.

Especially, these active compositions may contain adjuvant surfactants to enhance the deposition, wetting and penetration of the composition onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters of sulfosuccinic acids, ethoxylated organosilicones, ethoxylated fatty amines and blends of surfactant with mineral or vegetable oils. Mixtures of the above adjuvent systems can be employed to optimize the biological performance of the compounds of the present invention.

In such embodiments, the compounds of the present invention or compositions containing the same, can be advantageously employed in combination with one or more additional pesticidal compounds. Such additional pesticidal compounds may be insecticides, nematicides, miticides, arthropodicides, or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The exact amount of the active material to be applied is dependent not only on the specific active material being applied, but also on the particular action desired, the fungal species to be controlled and the stage of growth thereof as well as the part of the plant to be contacted with the toxic active ingredient. Thus, all of the active ingredients of the present invention and compositions containing the same may not be equally effective at similar concentrations or against the same fungal species.

The following active compounds set forth below in Table II were evaluated for fungicidal activity:

TABLE II

| Compound No. | Active Compound |
|---|---|
| 1 | 1,1-Dichloro-3-(3,5-dichlorophenyl)-3-hydroxy-4-(1,2,4-(1H)triazolyl)but-1-ene |
| 2 | 1,1-Dichloro-3-(2,4-dichlorophenyl)-3-hydroxy-4-(1,2,4-(1H)-triazolyl)but-1-ene |
| 3 | 1,1-Dichloro-3-(4-chlorophenyl)-3-hydroxy-4-(1,2,4-(1H)-triazolyl)but-1-ene |
| 4 | 1,1-Dichloro-3-(4-fluorophenyl)-3-hydroxy-4-(1,2,4-(1H)-triazolyl)but-1-ene |
| 5 | 1,1-Dichloro-3-phenyl-3-hydroxy-4-(1,2,4-(1H)triazolyl)but-1-ene |
| 6 | 1,1-Dichloro-3-(3,5-dichlorophenyl)-3-hydroxy-4-((1H)-imidazolyl)but-1-ene |
| 7 | 1,1-Dichloro-3-(4-fluorophenyl)-3-hydroxy-4-((1H)-imidazolyl)but-1-ene |

Representative formulations/compositions of the present invention include the following:

TABLE III

Emulsifiable Concentrate

| Ingredient | weight % of total composition |
|---|---|
| Compound of Example 3 | 10.0 |
| AGRILAN BM ® (a proprietary anionic/nonionic surfactant blend of Lankro Chemicals) | 5.0 |
| ATLOX 48518 ® (a proprietary anionic/nonionic surfactant blend of ICI Specialty Chemicals) | 5.0 |
| Dihydroisophorone | 80.0 |

TABLE IV

Wettable Powder

| Ingredient | weight % of total composition |
|---|---|
| Compound of Example 3 | 10.0 |
| AEROSOL OT-B ® (sodium dioctyl sulfosuccinate) | 1.0 |
| DYAPOL PT ® (a proprietary dispersing agent of Yorkshire Chemicals) | 5.0 |
| Barden Clay | 84.0 |

TABLE V

Flowable Concentrate

| Ingredient | weight % of total composition |
|---|---|
| Compound of Example 3 | 10.0 |
| AGRILAN F502 ® (a proprietary material of Lankro Chemicals) | 2.0 |
| DARVAN NO. 1 ® | 2.0 |

TABLE V-continued

Flowable Concentrate

| Ingredient | weight % of total composition |
|---|---|
| (a proprietary material of W. R. Grace & Co.) | |
| FOAMASTER UDB ® | 0.1 |
| (a proprietary material of Lankro Chemicals) | |
| DOWICIDE A ® | 0.05 |
| (a proprietary material of The Dow Chemical Co.) | |
| KELZAN ® | 0.1 |
| (a proprietary material of Kelco Co.) | |
| Propylene Glycol | 5.0 |
| Water | 80.75 |

TABLE VI

Dusts

| Ingredient | weight % of total composition |
|---|---|
| Compound of Example 3 | 1.0 |
| NEOSYL ® | 5.0 |
| (a proprietary material of J. Crosfields Co.) | |
| Barden Clay | 94.0 |

The method for evaluating in vivo fungicidal activity consists of applying the test compound, in diluted form, to a host plant. The plants are inoculated with the fungus (in spore form) and stored in a greenhouse or other controlled environment until untreated plants, used as controls, become infested with the fungus. The treated plants are then visually inspected and assigned a rating based on the percentage of total leaf area that has not become infested.

Formulations containing the test compounds are prepared from concentrates in acetone. The compound (0.04 g) was dissolved in 10 mL of acetone and 90 mL of water and 2 drops of a wetting agent were added to form a 400 ppm solution of the active compound for application to leaves or roots.

BARLEY POWDERY MILDEW

Procedure A: Soil Drench Test

Barley seeds cv Golden Promise were sown at a depth of ½ inch into 3-inch plastic pots (approximately 10 in each pot) containing sterilized loam soil. The pots were maintained under greenhouse conditions until the barley had germinated and reached a height of 3 to 5 inches. The test chemical (10 mL) was applied as a soil drench at a concentration of 400 ppm to each pot. The treated plants were held under greenhouse conditions for 24 hours and then inoculated with conidia of *Erysiphe graminis hordeii* by brushing the foliage with heavily sporulating plants. The plants were assessed for disease levels 10 days later by comparing the sporulation on plants treated with the experimental chemical to untreated but inoculated control plants.

Procedure B: Foliar Application

Barley was grown as for the above soil drench test. The foliage of the plants was sprayed with a 400 ppm solution of the test chemical. The treated plants were held under greenhouse conditions for 24 hours and then inoculated with conidia of *Erysiphe graminis hordeii* by brushing the foliage with heavily sporulating plants. The plants were assessed for disease levels 10 days later by comparing the sporulation on plants treated with the experimental chemical to untreated but inoculated control plants.

BARLEY SPOT BLOTCH

Procedure C: Soil Drench Test

Barley seeds cv Gerbel were sown at a depth of ½ inch into 3-inch plastic pots (approximately 10 in each pot) containing sterilized loam soil. The pots were maintained under greenhouse conditions until the barley had germinated and reached a height of 3 to 5 inches. The test chemical (10 mL) was applied as a soil drench at a concentration of 400 ppm to each pot. The treated plants were held under greenhouse conditions for 24 hours and then inoculated with conidia of *Cochliobolus sativus* by brushing the foliage with heavily sporulating plants. The plants were assessed for disease levels 7 days later by comparing the sporulation on plants treated with the experimental chemical to untreated but inoculated control plants.

Procedure D: Foliar Application

Barley was grown as for the above soil drench test. The foliage of the plants was sprayed with a 400 ppm solution of the test chemical. The treated plants were held under greenhouse conditions for 24 hours and then inoculated with conidia of *Cochliobolus sativus* by brushing the foliage with heavily sporulating plants. The plants were assessed for disease levels 7 days later by comparing the sporulation on plants treated with the experimental chemical to untreated but inoculated control plants.

BROWN RUST

Procedure E: Soil Drench Test

Wheat seeds cv Armada were sown at a depth of ½ inch into 3-inch plastic pots (approximately 10 in each pot) containing sterilized loam soil. The pots were maintained under greenhouse conditions until the barley had germinated and reached a height of 3 to 5 inches. The test chemical (10 mL) was applied as a soil drench at a concentration of 400 ppm to each pot. The treated plants were held under greenhouse conditions for 24 hours and then inoculated with a dense talc/spore suspension of *Puccinia recondita*. The plants were placed into a chamber with 100 percent relative humidity for 24 hours and then removed and held in a greenhouse for 7 days and assessed when symptoms of the disease appeared on untreated but inoculated control plants.

Procedure F: Foliar Application

Wheat was grown as for the above soil drench test. The foliage of the plants was sprayed with a 400 ppm solution of the test chemical. The treated plants were held under greenhouse conditions for 24 hours and then inoculated with a dense talc/spore suspension of *Puccinia recondita*. The plants were placed into a chamber with 100 percent relative humidity for 24 hours and then removed and held in a greenhouse for 7 days and assessed when symptoms of the disease appeared on the untreated but inoculated control plants.

RICE BLAST

Procedure G: Soil Drench Test

Barley seeds cv Golden Promise were sown at a depth of ½ inch into 3-inch plastic pots (approximately 10 in each pot) containing sterilized loam soil. The pots were maintained under greenhouse conditions until the barley had germinated and reached a height of 3 to 5 inches. The test chemical (10 mL) was applied as a soil drench at a concentration of 400 ppm to each pot. The treated plants were held under greenhouse conditions for 24 hours and then inoculated with $1\times10^6$ conidia per mL of *Pyricularia oryzae* (rice blast) by spraying the spores onto the leaves. The plants were placed into a chamber with 100 percent relative humidity for 48 hours and then removed and held in a greenhouse for 5 to 7 days and assessed when symptoms of the disease appeared on untreated but inoculated control plants.

Procedure H: Foliar Application

Barley was grown as for the above soil drench test. The foliage of the plants was sprayed with a 400 ppm solution of the test chemical. The treated plants were held under greenhouse conditions for 24 hours and then inoculated with $1\times10^6$ conidia per mL of *Pyricularia oryzae* (rice blast) by spraying the spores onto the leaves. The plants were placed into a chamber with 100 percent relative humidity for 48 hours and then removed and held in a greenhouse for 5 to 7 days and assessed when symptoms of the disease appeared on the untreated but inoculated control plants.

The results of test of procedures A, B, C, D, E, F, G and H are set forth hereinafter in Table VII.

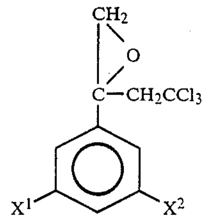

(IV)

wherein $X^1$ and $X^2$ are —Br, —Cl, or —$CH_3$ are taught in U.S. Pat. No. 4,211,549.

Those compounds corresponding to the formula

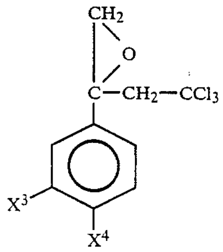

(V)

wherein each of $X^3$ and $X^4$ independently represents —H, —CN, nitro, alkoxy, —$CF_3$, benzyloxy or alkyl,

TABLE VII

| Comp. No.* | Percent control at 400 ppm of indicated organism: *Erysiphe graminis hordeii* soil | *Erysiphe graminis hordeii* foliar | *Puccinia recondita*** soil | *Puccinia recondita*** foliar | *Cochliobolus sativus* soil | *Cochliobolus sativus* foliar | *Pyricularia oryzae* soil | *Pyricularia oryzae* foliar |
|---|---|---|---|---|---|---|---|---|
| 1 | 95 | 85 | NT | <80 | 40 | 0 | NT | 75 |
| 2 | 100 | 100 | NT | NT | NT | NT | NT | 90 |
| 3 | 100 | 100 | 100 | 100 | NT | NT | NT | NT |
| 4 | NT | 100 | NT | NT | NT | NT | NT | 56 |
| 5 | NT | 100 | NT | NT | NT | NT | NT | 52 |
| | <80 | <80 | NT | <80 | NT | 80 | NT | <80 |
| | 100 | 100 | NT | <80 | NT | NT | NT | <80 |

*Compound Nos are the same as set forth in Table II.

**Test conducted employing a treating rate of 100 ppm.

The active compounds were also evaluated in in vitro test and found to be active against the following plants pathogenic species: *Alternaria brassisicola, Botrytis cinerea, Colletotrichum lindemuthianum, Fusarium oxysporum* fsp. *phaseolicola, Pyrenophora teres, Pythium ultimum, Sclerotium rolfsii,* and *Verticillium albo-atrum.*

When some of the compounds were applied at dosage levels of between 2.0 and 400.0 ppm, they had the ability to kill, inhibit or otherwise control one or more fungal diseases of plants.

STARTING MATERIALS

The oxirane compounds employed herein are for the most part well known compounds and those that are not specifically known can be prepared employing procedures analogous to those employed to prepare specifically known compounds.

Those compounds corresponding to the formula with the proviso that when $X^4$ is —H, $X^3$ is other than —H are taught in U.S. Pat. No. 4,018,801.

The compounds corresponding to the formula

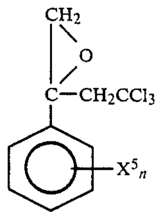

(VI)

wherein $X^5$ represents, in the 3, 4 or 5 ring position, —$CF_3$, alkyl, alkoxy, —Br, —Cl, —F or nitro and n represents an integer of from 0 to 3 can be prepared employing the same procedure as taught in U.S. Pat. No. 4,211,549 using the appropriate starting materials.

Those compounds corresponding to the formula

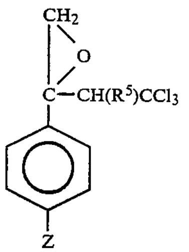

(VII)

wherein Z represents —H or —Cl and $R_3$ represents —H or straight chain alkyl are taught in Canadian Patent No. 527,462.

The compounds corresponding to the formula

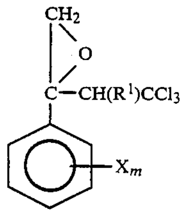

(III)

wherein $R^1$, X and m are as hereinabove set forth can be prepared employing the same procedure as taught in Canadian Patent No. 527,462 using the appropriate starting materials.

What is claimed is:

1. A substituted azole compound corresponding to the formulae

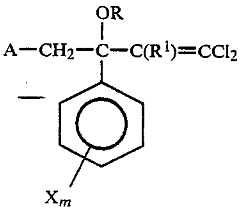

(Formula I)

wherein

A represents

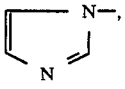, 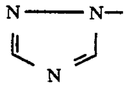 or 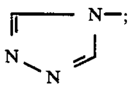;

R represents —H, $C_1$–$C_4$ alkyl, $C_1$–$C_4$ alkenyl, $C_1$–$C_4$ haloalkyl or —C(O)$R^2$;

$R^1$ represents —H, halo or $C_1$–$C_4$ straight chain alkyl;

$R^2$ represents $C_1$–$C_4$ alkyl, $C_1$–$C_2$ haloalkyl, phenyl, or phenyl substituted by lower alkyl or halo; each X independently represents —H, halo, —CN, $C_1$–$C_4$ alkyl, $C_1$–$C_4$ haloalkyl, $C_1$–$C_4$ alkoxy, $C_1$–$C_4$ alkoxy, $C_1$–$C_4$ alkoxysulfonyloxy, nitro or phenyl;

m represents 1 to 5; and the acid addition salts and metal complexes thereof.

2. A compound as defined in claim 1 wherein R represents —H or —C(O)$R^2$, $R^1$ is —H, $R^2$ is alkyl or haloalkyl, and X is —H or halo.

3. A compound as defined in claim 2 wherein m is 0, 1 or 2.

4. A compound as defined in claim 3 wherein R represents —H, $R^1$ is —H, and X is —H or halo.

5. A compound as defined in claim 4 wherein R is —H.

6. The compound as defined in claim 5 which is 1,1-dichloro-3-(3,5-dichlorophenyl)-3-hydroxy-4-((1H)-imidazolyl)but-1-ene.

7. The compound as defined in claim 5 which is 1,1-dichloro-3-(4-fluorophenyl)-3-hydroxy-4-((1H)-imidazolyl)but-1-ene.

8. A fungicidal composition which comprises an inert carrier in intimate admixture with a fungicidally effective amount of an active ingredient which is a substituted azole compound corresponding to the formulae

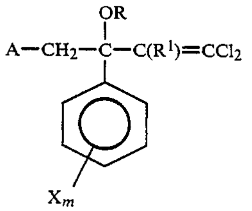

(Formula I)

wherein

A represents

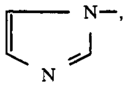, 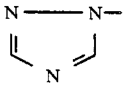 or 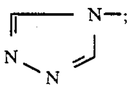;

R represents —H, $C_1$–$C_4$ alkyl, $C_1$–$C_4$ alkenyl, $C_1$–$C_4$ haloalkyl or —C(O)$R^2$;

$R^1$ represents —H, halo or $C_1$–$C_4$ straight chain alkyl;

$R^2$ represents $C_1$–$C_4$ alkyl, $C_1$–$C_2$ haloalkyl, phenyl, or phenyl substituted by lower alkyl or halo;

each X independently represents —H, halo, —CN, $C_1$–$C_4$ alkyl, $C_1$–$C_4$ haloalkyl, $C_1$–$C_4$ alkoxy, $C_1$–$C_4$ alkoxy, $C_1$–$C_4$ alkoxysulfonyloxy, nitro or phenyl;

m represents 1 to 5; and the acid addition salts and metal complexes thereof.

9. A composition as defined in claim 8 wherein R represents —H or —C(O)$R^2$, $R^1$ is —H, $R^2$ is alkyl or haloalkyl, and X is —H or halo.

10. A composition as defined in claim 9 wherein m is 0, 1 or 2.

11. A composition as defined in claim 10 wherein R represents —H, $R^1$ is —H, and X is —H or halo.

12. A composition as defined in claim 11 wherein R is —H.

13. The composition as defined in claim 12 wherein the active ingredient is 1,1-dichloro-3-(3,5-dichlorophenyl)-3-hydroxy-4-((1H)-imidazolyl)but-1-ene.

14. The composition as defined in claim 12 wherein the active ingredient is 1,1-dichloro-3-(4-fluorophenyl)-3-hydroxy-4-((1H)-imidazolyl)but-1-ene.

15. A method for the kill or control of fungal organisms which comprises contacting said organisms or their habitat with a fungicidal composition which comprises an inert carrier in intimate admixture with a fungicidally effective amount of an active ingredient which is a substituted azole compound corresponding to the formulae

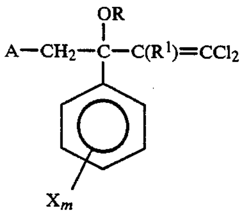

(Formula I)

wherein

A represents

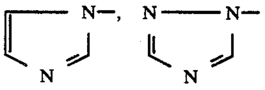 or 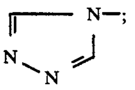

R represents —H, $C_1$–$C_4$ alkyl, $C_1$–$C_4$ alkenyl, $C_1$–$C_4$ haloalkyl or —C(O)$R^2$;

$R^1$ represents —H, halo or $C_1$–$C_4$ straight chain alkyl;

$R^2$ represents $C_1$–$C_4$ alkyl, $C_1$–$C_2$ haloalkyl, phenyl, or phenyl substituted by lower alkyl or halo;

each X independently represents —H, halo, —CN, $C_1$–$C_4$ alkyl, $C_1$–$C_4$ haloalkyl, $C_1$–$C_4$ alkoxy, $C_1$–$C_4$ alkoxy, $C_1$–$C_4$ alkoxysulfonyloxy, nitro or phenyl;

m represents 1 to 5; and the acid addition salts and metal complexes thereof.

16. A method as defined in claim 15 wherein R represents —H or —C(O)$R^2$, $R^1$ is —H, $R^2$ is alkyl or haloalkyl, and X is —H or halo.

17. A method as defined in claim 16 wherein m is 0, 1 or 2.

18. A method as defined in claim 17 wherein R represents —H, $R^1$ is —H, and X is —H or halo.

19. A method as defined in claim 18 wherein R is —H.

20. The method as defined in claim 19 wherein the active ingredient is 1,1-dichloro-3-(3,5-dichlorophenyl)-3-hydroxy-4-((1H)-imidazolyl)but-1-ene.

21. The method as defined in claim 19 wherein the active ingredient is 1,1-dichloro-3-(4-fluorophenyl)-3-hydroxy-4-((1H)-imidazolyl)but-1-ene.

* * * * *

UNITED STATES PATENT AND TRADEMARK OFFICE
CERTIFICATE OF CORRECTION

PATENT NO. : 4,927,833

DATED : May 22, 1990

INVENTOR(S) : Neil V. Kirby, Peter F.S. Street, Lowell D. Markley

It is certified that error appears in the above-identified patent and that said Letters Patent is hereby corrected as shown below:

Column 1, line 23, the bond should be through the ring.

Column 2, line 37, the bond should be through the ring.

Column 3, line 27, the bond should be through the ring.

Column 4, line 8, the bond should be through the ring.

Column 15, line 41, the bond should be through the ring.

Column 15, lines 48 through 51, delete the following formula:

" , 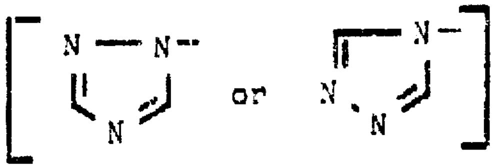 "

UNITED STATES PATENT AND TRADEMARK OFFICE
CERTIFICATE OF CORRECTION

PATENT NO. : 4,927,833

DATED : May 22, 1990

INVENTOR(S) : Neil V. Kirby, Peter F.S. Street, Lowell D. Markley

It is certified that error appears in the above-identified patent and that said Letters Patent is hereby corrected as shown below:

Column 16, line 25, the bond should be through the ring.

Column 16, lines 30 through 33, delete the following formula:

" , 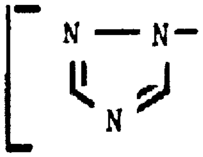 or 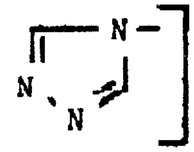 "

Column 17, line 8, the bond should be through the ring.

UNITED STATES PATENT AND TRADEMARK OFFICE
CERTIFICATE OF CORRECTION

PATENT NO. : 4,927,833

DATED : May 22, 1990

INVENTOR(S) : Neil V. Kirby, Peter F.S. Street, Lowell D. Markley

It is certified that error appears in the above-identified patent and that said Letters Patent is hereby corrected as shown below:

Column 17, lines 16 through 20, delete the following formula:

" , 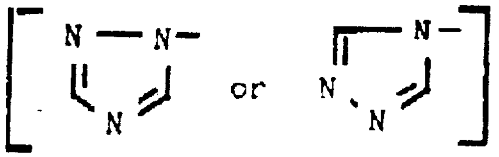 "

Signed and Sealed this

Twenty-fifth Day of June, 1991

Attest:

HARRY F. MANBECK, JR.

Attesting Officer

Commissioner of Patents and Trademarks